United States Patent [19]

Asselin et al.

[11] Patent Number: 4,521,423
[45] Date of Patent: Jun. 4, 1985

[54] 7,8,9,10-TETRAHYDROBENZO[h]QUINOLIN-9-AMINE DERIVATIVES AND COMPOSITIONS AND METHODS FOR TREATING DEPRESSION EMPLOYING THEM

[75] Inventors: Andre A. Asselin, St. Laurent, Canada; Leslie G. Humber, North Brunswick, N.J.

[73] Assignee: Ayerst, McKenna & Harrison, Ltd., Montreal, Canada

[21] Appl. No.: 547,318

[22] Filed: Oct. 31, 1983

[51] Int. Cl.³ .................... A61K 31/47; C07D 221/10
[52] U.S. Cl. .................................... 514/290; 546/101
[58] Field of Search .................. 546/101; 424/258; 260/244.4

[56] References Cited

U.S. PATENT DOCUMENTS 2,717,831  9/1955  Tulagin, et al. ............... 546/101 X
4,115,387  9/1978  Schwan .......................... 424/258

OTHER PUBLICATIONS

M. Abbasi et al., J. Heterocycl. Chem., 15, 649, (1978).
Chem. Abstr., 45, 2476g, (1951), for I. Iwai and S. Hara, J. Pharm. Soc. Japan, 70, 394, (1950).

Primary Examiner—Diana G. Rivers

[57] ABSTRACT

7,8,9,10-Tetrahydrobenzo[h]quinolin-9-amine derivatives of the formula

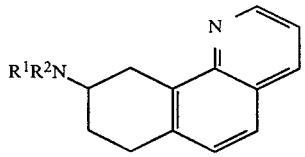

in which $R^1$ and $R^2$ each independently is hydrogen or lower alkyl, or $R^1$ and $R^2$ together form a chain of the formula —$(CH_2)_n$— where n is the integer 4, 5 or 6, are useful for treating depression.

4 Claims, No Drawings

7,8,9,10-TETRAHYDROBENZO[h]QUINOLIN-9-AMINE DERIVATIVES AND COMPOSITIONS AND METHODS FOR TREATING DEPRESSION EMPLOYING THEM

BACKGROUND OF THE INVENTION

This invention relates to 7,8,9,10-tetrahydrobenzo[h]quinolin-9-amine derivatives, to a process for their preparation, to pharmaceutical formulations thereof, and to a method of using the derivatives for treating depression.

7,8,9,10-Tetrahydrobenzo[h]quinolin-9-amine derivatives are a new class of compounds. Amino derivatives of benzo[h]quinolines have been reported previously; for example, see M. Abbasi et al., J. Heterocycl. Chem., 15, 649 (1978); V. Tulagin and R. F. Coles, U.S. Pat. No. 2,717,831, Sept. 13, 1955, and I. Iwai and S. Hara, J. Pharm. Soc. Japan, 70, 394 (1950). However, the present derivatives can be distinguished from the previously reported compounds because they have a completely different substitution pattern and/or they have a different degree of unsaturation in the ring system.

SUMMARY OF THE INVENTION

The compounds of the present invention are represented by formula

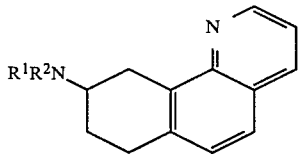

(I)

in which $R^1$ and $R^2$ each independently is hydrogen or lower alkyl, or $R^1$ and $R^2$ together form a chain of the formula —$(CH_2)_n$— wherein n is the integer 4, 5 or 6.

A preferred group of the compounds of the invention is represented by formula I wherein $R^1$ and $R^2$ each independently is lower alkyl.

Included within the scope of this invention are the therapeutically acceptable acid addition salts of the compounds of formula I.

The stereoisomers of the compounds of formula I also are included.

The compounds of formula I can be prepared by a process described herein.

A method is provided for treating depression in a mammal by administering to a mammal in need thereof an antidepression effective amount of the compound of formula I or a therapeutically acceptable acid addition salt.

The compound of formula I, or a therapeutically acceptable acid addition salt thereof, when admixed with a pharmaceutically acceptable carrier, forms a pharmaceutical composition which can be used according to the preceding method.

DETAILED DESCRIPTION OF THE INVENTION

The term "lower alkyl" as used herein means a straight chain alkyl radical containing from one to five carbon atoms or a branched chain alkyl radical containing three or four carbon atoms and includes methyl, ethyl, propyl, 1-methylethyl, butyl, 2-methylpropyl and 1,1-dimethylethyl. Preferred lower alkyl radicals contain from one to three carbon atoms.

The compounds of formula I are capable of forming acid addition salts with therapeutically acceptable acids.

The acid addition salts are prepared by reacting the base form of the appropriate compound of formula I with one or more equivalents preferably with an excess of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The useful antidepressant activity of the compounds of this invention can be demonstrated in standard pharmacological tests. For example, the ability of the present compounds to block substantially the uptake of norepinephrine and serotonin, characteristic properties of antidepressants, can be shown in the in vitro test using rat brain preparation as described by M. H. Kannengiesser, P. Hunt and J.-P. Raynaud, Biochem. Pharmacol., 22, 73 (1973); see also E. G. Shaskan and S. H. Snyder, J. Pharmacol. Exptl. Therap., 175, 404 (1970), and J. Glowinski and L. L. Iversen, J. Neurochemistry, 13, 655 (1966). In this test, for instance, 7,8,9,10-tetrahydro-N,N-dipropylbenzo[h]quinolin-9-amine dihydrochloride, described hereinafter, caused a 52% inhibition of [$^3$H]norepinephrine uptake at a concentration of $1\times10^{-6}$ moles, and caused a 57% inhibition of [$^3$H]serotonin uptake at a concentration of $1\times10^{-6}$ moles.

When the compounds of this invention are used to relieve the symptoms of depression in warm-blooded mammals, e.g. humans, rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 1.0 mg to about 30 mg per kilo per day, although as aforementioned variations will occur. However, a dosage level that is in the range of from about 1.0 mg to about 20 mg per kilo per day is most desirably employed in order to achieve effective results.

Unit dosage forms such as capsules, tablets, syrups, suspensions and the like may contain from 20 mg to about 200 mg of the active agent of this invention with a pharmaceutical carrier.

PROCESS FOR PREPARING THE COMPOUNDS

The compounds of this invention of formula I can be prepared by reacting a compound of formula II in which $R^1$ and $R^2$ are defined herein

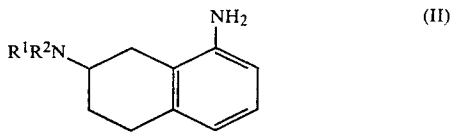

with glycerol in the presence of iodine and concentrated sulfuric acid. Preferably, an excess of each of glycerol, iodine and concentrated sulfuric acid is used. The reaction mixture is maintained at about 120° to 150° C. for about 30 minutes to three hours. Thereafter, the reaction mixture is cooled, rendered alkaline, and the corresponding compound of formula I is isolated from the mixture.

The starting materials of formula II are described by F.L.-E. Arvidsson et al. in World Patent Application (PCT) 81/03491, published Dec. 10, 1981 or they can be prepared by the methods described therein.

The following example illustrates further this invention.

EXAMPLE

Preparation of 7,8,9,10-Tetrahydro-N,N-dipropylbenzo[h]quinolin-9-amine (I: $R^1$ and $R^2$=CH$_3$CH$_2$CH$_2$)

A mixture of $N^7,N^7$-dipropyl-5,6,7,8-tetrahydro-1,7-naphthalenediamine (1.95 g, 0.008 mol), described by F.L.-E. Arvidsson et al., World Patent Application 81/03491, published Dec. 10, 1981, glycerol (4.7 mL, 0.064 mol) and iodine (0.05 g) was placed in a 250 mL round bottomed flask. The mixture was stirred at 20°-22° C. and concentrated sulfuric acid (6.5 mL, 0.120 mol) was added dropwise. The reaction soon commenced and the temperature rose to 70° C. and stayed at that point until the addition was complete. The flask was heated to 140° C. in an oil bath for 30 minutes. The reaction proceeded with evolution of SO$_2$ and some iodine vapor. Thereafter, the reaction mixture was cooled to 20°-22° C. and then rendered alkaline by the dropwise addition of concentrated NH$_4$OH. The mixture was extracted with chloroform. Insoluble polymeric material in the extract was removed by filtering the extract through a bed of diatomaceous earth. The filtrate was evaporated to dryness. The residue was taken up in diethyl ether. The solution was passed through a column of magnesium silicate, and the column washed with diethyl ether. The combined eluate was evaporated to give the title compound as a colorless oil. Treatment of the oil with a solution of HCl in diethyl ether, followed by recrystallization of the resulting solid from methanol gave the trihydrochloride salt of the title compound having mp 249°-255° C.; Anal. Calcd for C$_{19}$H$_{26}$N$_2$.3HCl; C, 58.40% H, 7.48% N, 7.16%; Found: C, 58.62%, H, 7.22% N, 7.22%; the NMR (CDCl$_3$) of the free base exhibited δ1.04 (t, 3H), 1.06 (t, 3H), 2.05 (m, 6H), 3.25 (m, 8H), 4.22 and 4.40 (m, 1H), 7.65 (d, J=8 Hz, 1H), 7.87 (2d, J=8 Hz, 1H), 7.95 (d, J=8 Hz, 1H), 8.88 (2d, J=8 Hz, J=1.5 Hz, 1H), 9.19 (2d, J=8 Hz, J=1.5 Hz, 1H), 11.0 (broad, 2H).

By substituting other appropriate N,N-dialkyl-tetrahydronaphthalenediamine derivatives, disclosed by Arvidsson et al., for $N^7,N^7$-dipropyl-5,6,7,8-tetrahydro-1,7-naphthalenediamine, other compounds of formula I are obtainable.

We claim:

1. A compound of the formula

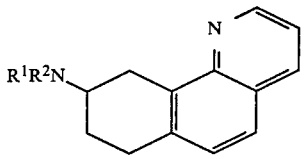

in which $R^1$ and $R^2$ each independently is lower alkyl, or a therapeutically acceptable acid addition salt thereof.

2. The compound of claim 1, which is 7,8,9,10-tetrahydro-N,N-dipropylbenzo[h]quinolin-9-amine.

3. A pharmaceutical composition in unit dosage form for treating depression which comprises the compound of claim 1, or a therapeutically acceptable acid addition salt thereof, and a pharmaceutically acceptable carrier.

4. A method for treating depression comprising administering to a host in need thereof an antidepression effective unit of the compound of claim 1.

* * * * *